(12) United States Patent
Yu et al.

(10) Patent No.: US 11,216,549 B2
(45) Date of Patent: Jan. 4, 2022

(54) SECURITY VERIFICATION METHOD AND DEVICE

(71) Applicant: HUAWEI TECHNOLOGIES CO., LTD., Shenzhen (CN)

(72) Inventors: Shangchun Yu, Xi'an (CN); Weihua Hu, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 288 days.

(21) Appl. No.: 16/344,016

(22) PCT Filed: Oct. 21, 2016

(86) PCT No.: PCT/CN2016/102965
§ 371 (c)(1),
(2) Date: Apr. 22, 2019

(87) PCT Pub. No.: WO2018/072215
PCT Pub. Date: Apr. 26, 2018

(65) Prior Publication Data
US 2019/0340348 A1 Nov. 7, 2019

(51) Int. Cl.
*A61B 5/00* (2006.01)
*G06F 1/16* (2006.01)
(Continued)

(52) U.S. Cl.
CPC ............ *G06F 21/35* (2013.01); *A61B 5/681* (2013.01); *G06F 1/163* (2013.01); *G06F 1/1698* (2013.01); *H04W 4/80* (2018.02)

(58) Field of Classification Search
CPC ...... G06F 3/0488; G06F 1/163; G06F 1/1698; G06F 21/35; A61B 5/684; A61B 5/681; H04W 4/80
See application file for complete search history.

(56) References Cited

U.S. PATENT DOCUMENTS

2014/0366123 A1* 12/2014 DiBona .................. G06Q 10/00
726/16
2015/0381609 A1* 12/2015 Dadu .................. H04W 12/065
726/9
(Continued)

FOREIGN PATENT DOCUMENTS

| CN | 104363987 A | 2/2015 |
| CN | 104850769 A | 8/2015 |
| CN | 105122151 A | 12/2015 |
| CN | 105143996 A | 12/2015 |

(Continued)

*Primary Examiner* — Vu V Tran
(74) *Attorney, Agent, or Firm* — Maier & Maier, PLLC

(57) ABSTRACT

Embodiments of the present invention provide a security verification method and a device, and relate to the field of communications technologies, so as to verify a user identity based on a wearing status monitoring result and a pairing result of the device. The method includes: monitoring, by a first device, a pairing status of the first device and a second device and/or a wearing status of the first device; receiving a user operation instruction, where the instruction includes information about an interface operated by a user; when it is determined, based on the information about the interface, that the interface is an access-restricted interface, determining a wearing status and/or a pairing status of the first device within a verification time window; determining, based on the wearing status and/or the pairing status within the verification time window, whether the first device is in a secure state; and locking the interface if the first device is in an insecure state; or responding to the user operation instruction if the first device is in the secure state.

15 Claims, 7 Drawing Sheets

First device

Second device

Wireless connection

(51) Int. Cl.
*G06F 3/0488* (2013.01)
*G06F 21/35* (2013.01)
*H04W 4/80* (2018.01)

(56) References Cited

U.S. PATENT DOCUMENTS

| | | | |
|---|---|---|---|
| 2016/0378100 A1* | 12/2016 | Dow | G06F 1/163 |
| | | | 700/275 |
| 2016/0379205 A1* | 12/2016 | Margadoudakis | ............................ |
| | | | G06Q 30/0601 |
| | | | 705/71 |
| 2017/0150305 A1* | 5/2017 | Chaudhri | H04B 1/385 |
| 2017/0200014 A1 | 7/2017 | Jing | |
| 2019/0230507 A1* | 7/2019 | Li | H04L 9/3231 |
| 2021/0110019 A1* | 4/2021 | Ko | H04W 12/065 |

FOREIGN PATENT DOCUMENTS

| | | |
|---|---|---|
| CN | 105487669 A | 4/2016 |
| CN | 105812584 A | 7/2016 |
| EP | 2 956 825 B1 | 6/2020 |
| KR | 20160002520 A | 1/2016 |
| WO | 2014143997 A1 | 9/2014 |

\* cited by examiner

SECURITY VERIFICATION METHOD AND DEVICE

CROSS-REFERENCE TO RELATED APPLICATIONS

This application is a national stage of International Application No. PCT/CN2016/102965, filed on Oct. 21, 2016, which is hereby incorporated by reference in its entirety.

TECHNICAL FIELD

The present invention relates to the field of communications technologies, and in particular, to a security verification method and a device.

BACKGROUND

Currently, wearable devices are widely used, and more functions of the wearable devices are diversified, for example, exercise and health monitoring, incoming call reminding, and offline scan-payment. With a continuous increase in functions of the wearable devices, privacy, information security, capital security, and the like of a consumer are at increasingly high risk. For example, a capital loss is caused if a wearable device is lost and a person other than an owner completes scan-payment by using the device.

Therefore, it is necessary to perform security verification on the wearable device, so that an unauthorized user cannot operate a sensitive function (for example, offline payment) or view sensitive information (such as an SMS message, an instant messaging message, and health data). Security verification is usually performed on an existing wearable device by locking a screen by using a password or a pattern. A user needs to successfully unlock the screen to operate a sensitive function, view sensitive information, or the like However, a password unlocking mechanism or a pattern locking mechanism has a relatively high configuration (for example, a screen size, touch performance, and a supported input method) requirement on a wearable device, and cannot be applied to all wearable devices. For example, a band product without a screen cannot support a digit input unlocking mechanism or a pattern unlocking mechanism.

It can be learned that an existing security verification method of the wearable device is applicable to a limited range, and a security verification mechanism that is applicable to a wider range needs to be provided.

SUMMARY

Embodiments of the present invention provide a security verification method and a device. Whether a device is in a secure state is determined based on a wearing status monitoring result and a pairing status monitoring result of the device, so as to ensure access security with lower hardware and software costs. The method is applicable to a device without a screen or a low-configuration device that has a screen but is incapable of supporting a security verification manner based on a password, a pattern, or the like.

To achieve the foregoing objectives, the following technical solutions are used in the embodiments of the present invention.

According to a first aspect, a security verification method is disclosed, including: monitoring, by a near field communication chip of a first device in real time, a pairing status of the first device and a second device, and/or monitoring, by a sensor of the first device in real time, a wearing status of the first device; receiving, by the first device, a user operation instruction, where the instruction includes information about an interface operated by a user; if the first device determines, based on the information about the interface, that the interface is an access-restricted interface, determining a wearing status and/or a pairing status of the first device within a verification time window; determining, based on the wearing status and/or the pairing status within the verification time window, whether the first device is in a secure state; and locking the interface if it is determined that the first device is in an insecure state; or responding to the user operation instruction if it is determined that the first device is in the secure state. The verification time window is duration between a moment at which the user operation instruction is received and a latest moment at which it is determined that the first device is in the secure state, or duration between a moment at which the user operation instruction is received and a moment at which a security verification function of the first device is enabled for the first time.

In a specific implementation, the first device monitors in real time the pairing status and/or the wearing status of the first device. When a user operates the first device (for example, a smart wearable device), for example, touches a screen or presses a key, the first device receives a user operation instruction entered by the current user. To avoid a privacy disclosure and a capital loss caused because the device is lost, the pairing status and/or the wearing status of the device within a time period may be determined, so as to determine, based on the pairing status and/or the wearing status of the wearable device, whether the first device is in the secure state. It can be learned that a configuration requirement on the wearable device is not high in the verification method, and identity verification can be performed on a user of the device by using a wearing monitoring module and a wireless connection module (for example, a Bluetooth module) configured on most devices. The method is applicable to most wearable devices, especially a low-configuration device without a screen, and may be used to verify a user identity, so as to significantly avoid a user loss after such wearable devices are lost or stolen.

With reference to the first aspect, in a first possible implementation of the first aspect, the determining, by the first device based on the wearing status or the pairing status within the verification time window, whether the first device is in a secure state specifically includes: if the first device is in a worn state within the verification time window, determining that the first device is in the secure state.

If the first device is not taken off all the time within the verification time window or is taken off for an extremely short time within the verification time window, it may be considered that the first device is in the worn state. In this case, it may be considered that the user of the first device remains unchanged, and the first device is currently in the secure state and may respond to the user operation instruction.

With reference to the first aspect, in a second possible implementation of the first aspect, the determining, by the first device based on the wearing status or the pairing status within the verification time window, whether the first device is in a secure state specifically includes: if the first device is in a paired state within the verification time window, determining whether a pairing object of the first device has changed; and if the pairing object of the first device remains unchanged, determining that the first device is in the secure state; or if the pairing object of the first device has changed, determining that the first device is in the insecure state.

The pairing object herein may be information about the second device or user information entered by the user by using a management application program of the second device. When the information about the second device paired with the first device remains unchanged, or user information paired with the first device remains unchanged, it indicates that the user of the first device remains unchanged, and it may be considered that the first device is in the secure state. In addition, if the first device is in the paired state within the verification time window, but the pairing object has changed, the user of the first device may have changed, so that the first device is in the insecure state.

With reference to the first aspect, in a third possible implementation of the first aspect, the determining, by the first device based on the wearing status or the pairing status within the verification time window, whether the first device is in a secure state specifically includes: if the first device is in a non-worn state and a paired state within the verification time window, determining whether a pairing object of the first device has changed; and if it is determined that the pairing object of the first device remains unchanged, determining that the first device is in the secure state; or if it is determined that the pairing object of the first device has changed, determining that the first device is in the insecure state.

An application state of the first device is the non-worn state and the paired state, that is, the first device is still paired with a second device although the first device is taken off. Therefore, whether the paired second device (or user information) has changed needs to be determined. If the pairing object (the information about the second device or the user information) has changed, the first device may be lost or stolen, and another person connects another terminal to the first device to log in to a corresponding management application program. In this case, it may be considered that the user of the first device has changed, and the first device is in the insecure state.

With reference to the first aspect, in a fourth possible implementation of the first aspect, if the first device is in a non-worn state and an unpaired state within the verification time window, the first device obtains information about a current pairing object, determines, based on the information about the current pairing object, whether a pairing object of the first device has changed, and if determining that the pairing object of the first device has changed, determines that the first device is in the insecure state; or if determining that the pairing object of the first device remains unchanged, determines that the first device is in the secure state.

When the first device is taken off or is taken off for a long time, it may be determined that the first device is in the non-worn state. If a wireless connection between the first device and the second device is broken (for example, the Bluetooth is disabled), it may be determined that the first device is in the unpaired state. In this case, because the first device is taken off and is disconnected from the second device, it is uncertain whether a current pairing second device is an initially paired second device (or whether user information is initially entered user information), and the information about the current pairing object needs to be obtained to determine whether the pairing object has changed.

With reference to the fourth possible implementation of the first aspect, in a fifth possible implementation of the first aspect, the obtaining, by the first device, information about a current pairing object specifically includes: prompting, by the first device, a pairing reminder message, where the pairing reminder message is used to prompt the user to trigger a current pairing second device to establish a wireless connection to the first device; establishing, by the first device, a wireless connection to the current pairing second device; and receiving the information that is about the current pairing object and that is sent by the current pairing second device, where the information about the current pairing object is information about the current pairing second device or user information corresponding to the current pairing second device.

The user information corresponding to the second device herein is user information entered by a user by using a management application program of the second device. The second device needs to be triggered to interact with the first device because it is uncertain whether the current pairing second device has changed. In this case, the first device may establish a wireless connection to the second device, to obtain the information about the second device or the user information corresponding to the second device, and determine whether the user of the first device has changed, so as to further determine whether the first device is in the secure state.

With reference to the fifth possible implementation of the first aspect, in a sixth possible implementation of the first aspect, the determining, by the first device based on the information about the current pairing object, whether a pairing object of the first device has changed specifically includes: determining, by the first device, whether the information about the current pairing object is the same as information about an initial pairing object; and if the information about the current pairing object is the same as the information about the initial pairing object, determining that the pairing object of the first device remains unchanged; or if the information about the current pairing object is different from the information about the initial pairing object, determining that the pairing object of the first device has changed.

With reference to the sixth possible implementation of the first aspect, in a seventh possible implementation of the first aspect, if the information about the initial pairing object is information about a second device initially paired with the first device, the information about the current pairing object is the information about the current pairing second device; or if the information about the initial pairing object is user information corresponding to a second device initially paired with the first device, the information about the current pairing object is the user information corresponding to the current pairing second device.

In a specific implementation, if the pairing object is a second device, whether the user of the first device has changed is determined by determining whether the current pairing second device is the initially paired second device, and current verification information is the information about the current pairing second device. Further, if the information about the current pairing second device is the same as the information about the initially paired second device, it is considered that the second device paired with the first device remains unchanged, and the user of the first device also remains unchanged. If the pairing object is user information, whether the user of the first device has changed is determined by determining whether currently paired user information is initially paired user information, and current verification information is user information entered by a current user (that is, the user information corresponding to the current pairing second device). Further, if user information entered by an initial user by using the initially paired second device (that is, the user information corresponding to the second device initially paired with the first device) is the same as user information entered by the current user by using the current pairing second device. It may be considered that a terminal paired with the first device remains unchanged, and the user of the wearable device remains unchanged.

According to a second aspect, a first device is disclosed, including:

a monitoring unit, configured to monitor a pairing status of the first device and a second device and/or a wearing status of the first device; a receiving unit, configured to receive a user operation instruction, where the user operation instruction includes information about an interface operated by a user; a determining unit, configured to: when determining, based on the information about the interface, that the interface is an access-restricted interface, determine a wearing status and/or a pairing status of the first device within a verification time window; a judging unit, configured to determine, based on the wearing status and/or the pairing status within the verification time window and determined by the determining unit, whether the first device is in a secure state; and a permission control unit, configured to lock the interface when the judging unit determines that the first device is in an insecure state, or respond to the user operation instruction when the judging unit determines that the first device is in the secure state. The verification time window is duration between a moment at which the user operation instruction is received and a latest moment at which it is determined that the first device is in the secure state, or duration between a moment at which the user operation instruction is received and a moment at which a security verification function of the first device is enabled for the first time.

With reference to the second aspect, in a first possible implementation of the second aspect, the judging unit is specifically configured to: if the first device is in a worn state within the verification time window, determine that the first device is in the secure state.

With reference to the second aspect, in a second possible implementation of the second aspect, the judging unit is specifically configured to: if the first device is in a paired state within the verification time window, determine whether a pairing object of the first device has changed; and if the pairing object of the first device remains unchanged, determine that the first device is in the secure state; or if the pairing object of the first device has changed, determine that the first device is in the insecure state.

With reference to the second aspect, in a third possible implementation of the second aspect, the judging unit is specifically configured to:

if the first device is in a non-worn state and a paired state within the verification time window, determine whether a pairing object of the first device has changed; and if determining that the pairing object of the first device remains unchanged, determine that the first device is in the secure state; or if determining that the pairing object of the first device has changed, determine that the first device is in the insecure state.

With reference to the second aspect, in a fourth possible implementation of the second aspect, the first device further includes an obtaining unit, where if the judging unit specifically determines that the first device is in a non-worn state and an unpaired state within the verification time window, the obtaining unit is configured to obtain information about a current pairing object;

the judging unit is further configured to determine, based on the information about the current pairing object, whether a pairing object of the first device has changed; and the judging unit is configured to: if determining that the pairing object of the first device has changed, determine that the first device is in the insecure state; or if determining that the pairing object of the first device remains unchanged, determine that the first device is in the secure state.

With reference to the fourth possible implementation of the second aspect, in a fifth possible implementation of the second aspect, the obtaining unit is specifically configured to: prompt a pairing reminder message, where the pairing reminder message is used to prompt the user to trigger a current pairing second device to establish a wireless connection to the first device;

establish a wireless connection to the current pairing second device, and receive the information that is about the current pairing object and that is sent by the current pairing second device, where the information about the current pairing object is information about the current pairing second device or user information corresponding to the current pairing second device.

With reference to the fifth possible implementation of the second aspect, in a sixth possible implementation of the second aspect, the judging unit is specifically configured to: determine whether the information about the current pairing object is the same as information about an initial pairing object; and if the information about the current pairing object is the same as the information about the initial pairing object, determine that the pairing object of the first device remains unchanged; or if the information about the current pairing object is different from the information about the initial pairing object, determine that the pairing object of the first device has changed.

With reference to the sixth possible implementation of the second aspect, in a seventh possible implementation of the second aspect, if the information about the initial pairing object is information about a second device initially paired with the first device, the information about the current pairing object is the information about the current pairing second device; or if the information about the initial pairing object is user information corresponding to a second device initially paired with the first device, the information about the current pairing object is the user information corresponding to the current pairing second device.

According to a third aspect, a first device is disclosed, including:

a near field communication chip, configured to monitor a pairing status of the first device and a second device; and/or a sensor, configured to monitor a wearing status of the first device; an input component, configured to receive a user operation instruction, where the user operation instruction includes information about an interface operated by a user; and a processor, configured to: when determining, based on the information about the interface, that the interface is an access-restricted interface, determine a wearing status and/or a pairing status of the first device within a verification time window; determine, based on the wearing status and/or the pairing status within the verification time window and determined by the determining unit, whether the first device is in a secure state; and lock the interface when the judging unit determines that the first device is in an insecure state, or respond to the user operation instruction when the judging unit determines that the first device is in the secure state. The verification time window is duration between a moment at which the user operation instruction is received and a latest moment at which it is determined that the first device is in the secure state, or duration between a moment at which the user operation instruction is received and a moment at which a security verification function of the first device is enabled for the first time.

With reference to the third aspect, in a first possible implementation of the third aspect, the processor is specifically configured to: if the first device is in a worn state within the verification time window, determine that the first device is in the secure state.

With reference to the third aspect, in a second possible implementation of the third aspect, the processor is specifically configured to: if the first device is in a paired state within the verification time window, determine whether a pairing object of the first device has changed; and if the pairing object of the first device remains unchanged, determine that the first device is in the secure state; or if the pairing object of the first device has changed, determine that the first device is in the insecure state.

With reference to the third aspect, in a third possible implementation of the third aspect, the processor is specifically configured to: if the first device is in a non-worn state and a paired state within the verification time window, determine whether a pairing object of the first device has changed; and if determining that the pairing object of the first device remains unchanged, determine that the first device is in the secure state; or if determining that the pairing object of the first device has changed, determine that the first device is in the insecure state.

With reference to the third aspect, in a fourth possible implementation of the third aspect, the processor is specifically configured to: if the first device is in a non-worn state and an unpaired state within the verification time window, obtain information about a current pairing object; and the processor is further configured to: determine, based on the information about the current pairing object, whether a pairing object of the first device has changed; and if determining that the pairing object of the first device has changed, determine that the first device is in the insecure state; or if determining that the pairing object of the first device remains unchanged, determine that the first device is in the secure state.

With reference to the fourth possible implementation of the third aspect, in a fifth possible implementation of the third aspect, the first device further includes an output component, where the output component is specifically configured to prompt a pairing reminder message, where the pairing reminder message is used to prompt the user to trigger a current pairing second device to establish a wireless connection to the first device; and the near field communication chip is configured to establish a wireless connection to the current pairing second device, and receive the information that is about the current pairing object and that is sent by the current pairing second device, where the information about the current pairing object is information about the current pairing second device or user information corresponding to the current pairing second device.

With reference to the fifth possible implementation of the third aspect, in a sixth possible implementation of the third aspect, the processor is specifically configured to: determine whether the information about the current pairing object is the same as information about an initial pairing object; and if the information about the current pairing object is the same as the information about the initial pairing object, determine that the pairing object of the first device remains unchanged; or if the information about the current pairing object is different from the information about the initial pairing object, determine that the pairing object of the first device has changed.

With reference to the sixth possible implementation of the third aspect, in a seventh possible implementation of the third aspect, if the information about the initial pairing object is information about a second device initially paired with the first device, the information about the current pairing object is the information about the current pairing second device; or if the information about the initial pairing object is user information corresponding to a second device initially paired with the first device, the information about the current pairing object is the user information corresponding to the current pairing second device.

DESCRIPTION OF EMBODIMENTS

The following clearly and completely describes the technical solutions in the embodiments of the present invention with reference to the accompanying drawings in the embodiments of the present invention. Apparently, the described embodiments are merely some but not all of the embodiments of the present invention. All other embodiments obtained by a person of ordinary skill in the art based on the embodiments of the present invention without creative efforts shall fall within the protection scope of the present invention.

Currently, a wearable device may be used to implement exercise and health monitoring, incoming call reminding, information pushing and viewing, offline scan-payment, and the like. Existing quick payment supports offline scan-payment. Specifically, the wearable device generates a payment code (such as a bar code or a QR code). A merchant can complete payment by scanning the payment code. The wearable device does not need to access the Internet in a payment process.

In this case, security verification needs to be performed on a user of the wearable device, so as to avoid that an unauthorized user operates a sensitive function such as offline payment, which may cause a user loss. Currently, an unlock interface may be displayed on a screen of the wearable device, and receives an unlocking password or an unlocking gesture entered by a user, so as to perform identity verification on the user. However, this verification mechanism is applicable to only a high-configuration wearable device with a screen. For a wearable device without a screen, this mechanism cannot be used to perform security verification on a user.

Embodiments of the present invention provide an identity verification method. When a first device and a second device are paired for use, security verification may be performed on a user of the first device by monitoring a wearing status and a Bluetooth connection status of the first device. If the user of the first device has changed, it is forbidden to operate the first device. In this way, for any type of wearable devices, especially a low-configuration wearable device without a screen, verification can be performed on a user identity based on a wearing status monitoring result, so as to avoid a privacy disclosure, a capital loss, or the like caused because the device is lost or stolen.

Figure 1:
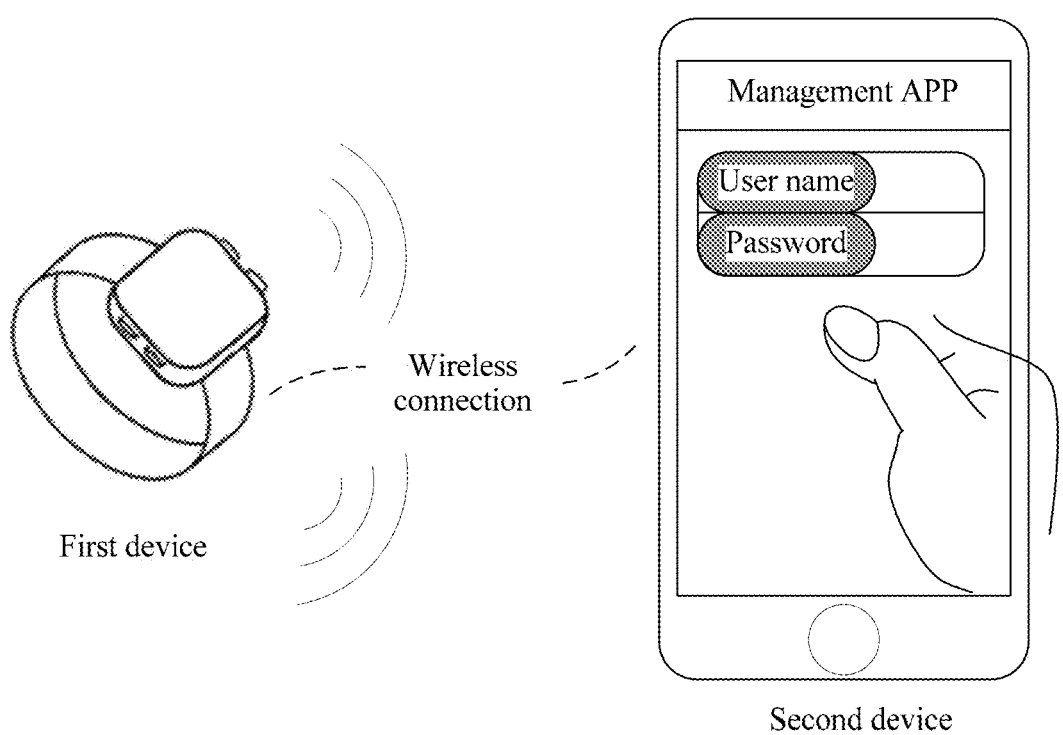
FIG. 1 is a schematic diagram of a device management system according to an embodiment of the present invention.

An embodiment of the present invention provides a device management system. As shown in FIG. 1, a first device may be a device without a screen, a device with a screen but cannot support a security verification manner that is based on a password, a pattern, or the like, or a terminal device that needs to perform security verification, such as a mobile phone, a smart wearable product, or a wireless network device. A second device may be a personal terminal such as a mobile phone or a tablet computer, or may be a smart wearable device. A user may simultaneously use the first device and the second device, and the first device may establish a wireless connection such as a Bluetooth connection to the second device. In addition, the second device may have a management application program (such as a management APP) that is corresponding to the first device and that is used to manage the first device. After the first device is connected to the second device, the management application program may act as a medium of information interaction between the second device and the first device. For example, a user enters user information (such as a user name and a password) on a login page of the management application program. The management application program invokes an interface of the second device, and sends, by using the wireless connection between the second device and the first device, the user information received on the login page to the first device. In this way, the first device obtains the user information of the user.

Figure 2:
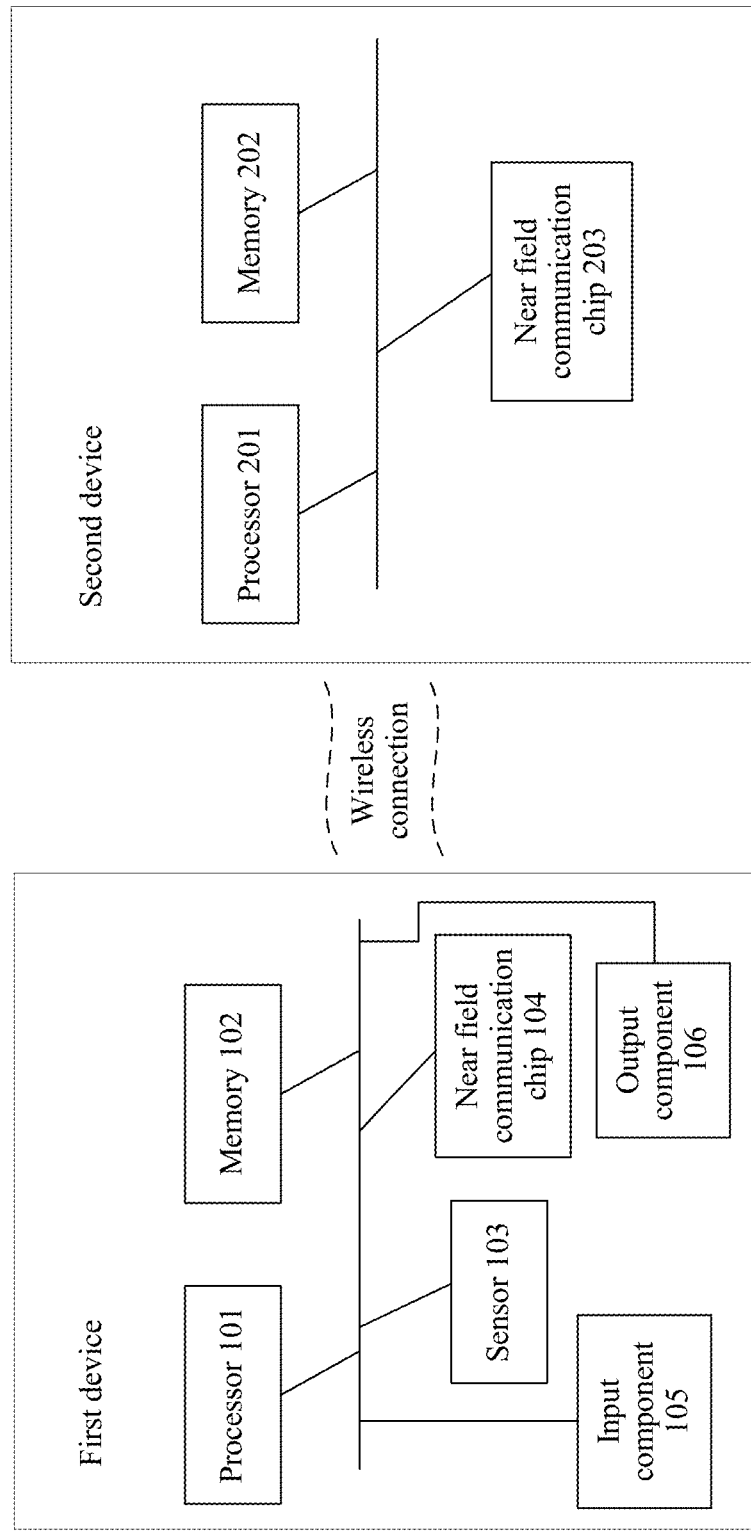
FIG. 2 is a schematic diagram of a first device and a second device according to an embodiment of the present invention.

Further, as shown in FIG. 2, a first device 1 includes at least a processor 101, a memory 102, a sensor 103, a near field communication chip 104, an input component 105, and an output component 106. A second device 2 includes at least a processor 201, a memory 202, and a near field communication chip 203. The input component 105 may be a microphone, a key, a touch panel, or the like. The output component 106 may be a microphone, a touch panel, an indicator, or the like. The near field communication chip 104 and the near field communication chip 203 may be a Bluetooth chip, an NFC (Near Field Communication, near field communication) chip, or the like.

The sensor is configured to monitor, in real time, a wearing status of the first device, including a worn state or a non-worn state, for example, monitor whether the first device is worn on a wrist (or certainly another body part, which is not limited herein). The near field communication chip is configured to establish a Bluetooth connection between the first device and the second device, and may further record a pairing status of the first device and the second device, and the pairing status includes a paired state or an unpaired state.

In a specific implementation, a security verification function key is disposed on the first device. A security verification function is enabled or disabled by default when the first device is delivered from a factory. A user enables or disables the security verification function by using the security verification function key of the first device.

After the first device is powered on, the sensor starts to monitor the wearing status of the first device, and the Bluetooth chip starts to monitor the pairing status of the first device and the second device. When monitoring that the security verification function is enabled for the first time, the processor of the first device records information about the second device paired with the first device or user information corresponding to the second device. The information about the second device may be an SN (Serial Number, serial number), a MAC (Media Access Control or Medium Access Control, media access control) address, an IMEI (International Mobile Equipment Identity, international mobile equipment identity), or the like of the second device. The user information corresponding to the second device is user information entered by the user into a management application program of the second device, and may be an account and a password, an identity, or the like. It should be noted that if security verification is performed on the first device, when a security verification result of the first device is a secure state, the first device updates the previously recorded information about the second device (or the previously recorded user information corresponding to the second device) to information about a currently paired second device (or user information corresponding to a currently paired second device). The previously recorded information about the second device is information that is about the second device and that is monitored from a moment at which the verification function of the first device is enabled to a current moment, or information that is about the second device and that is monitored from a moment at which a latest verification success result is obtained to a current moment.

Embodiment 1

Figure 3A:
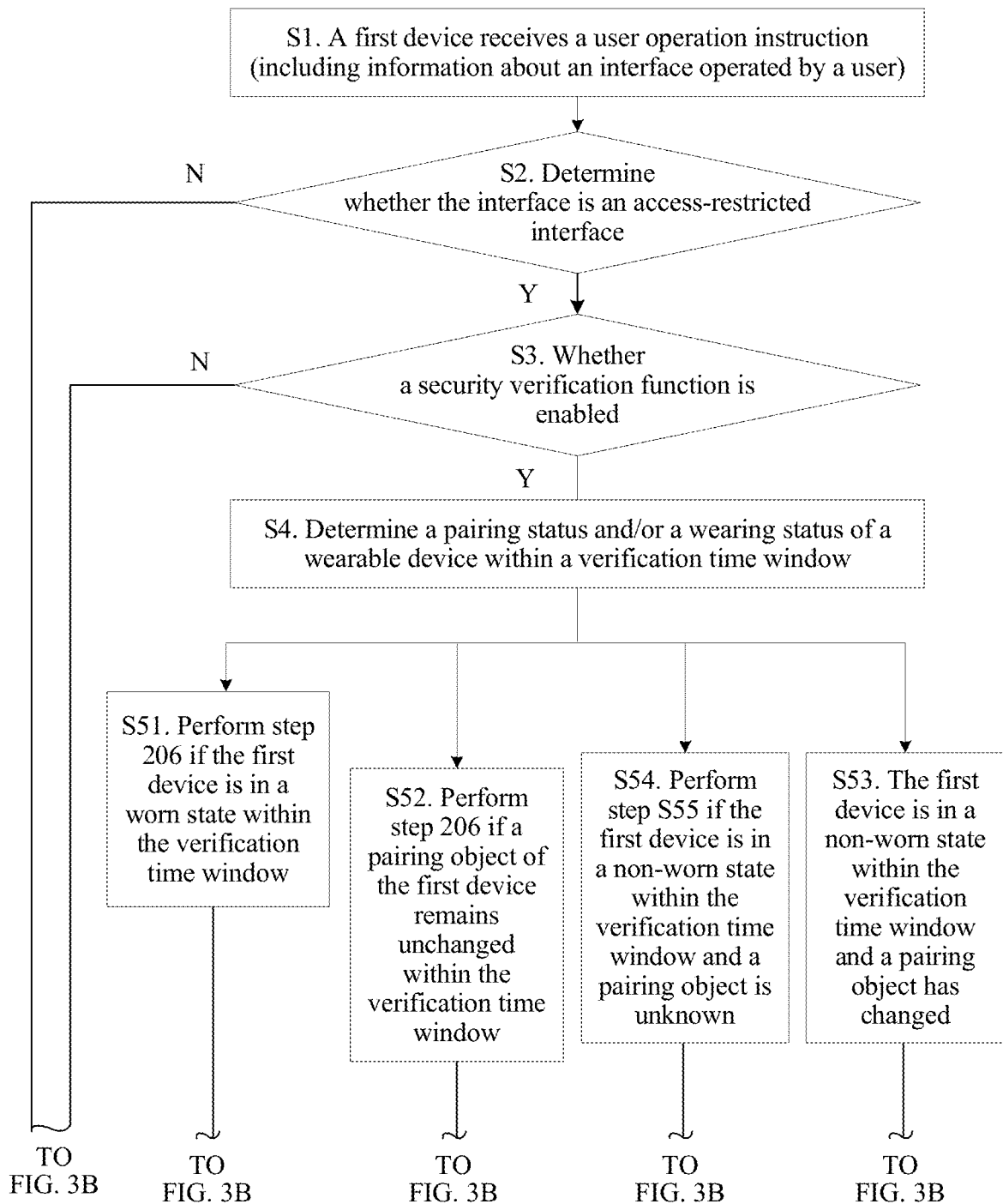
FIG. 3A and FIG. 3B are a schematic flowchart of a security verification method according to an embodiment of the present invention.
Figure 3B:
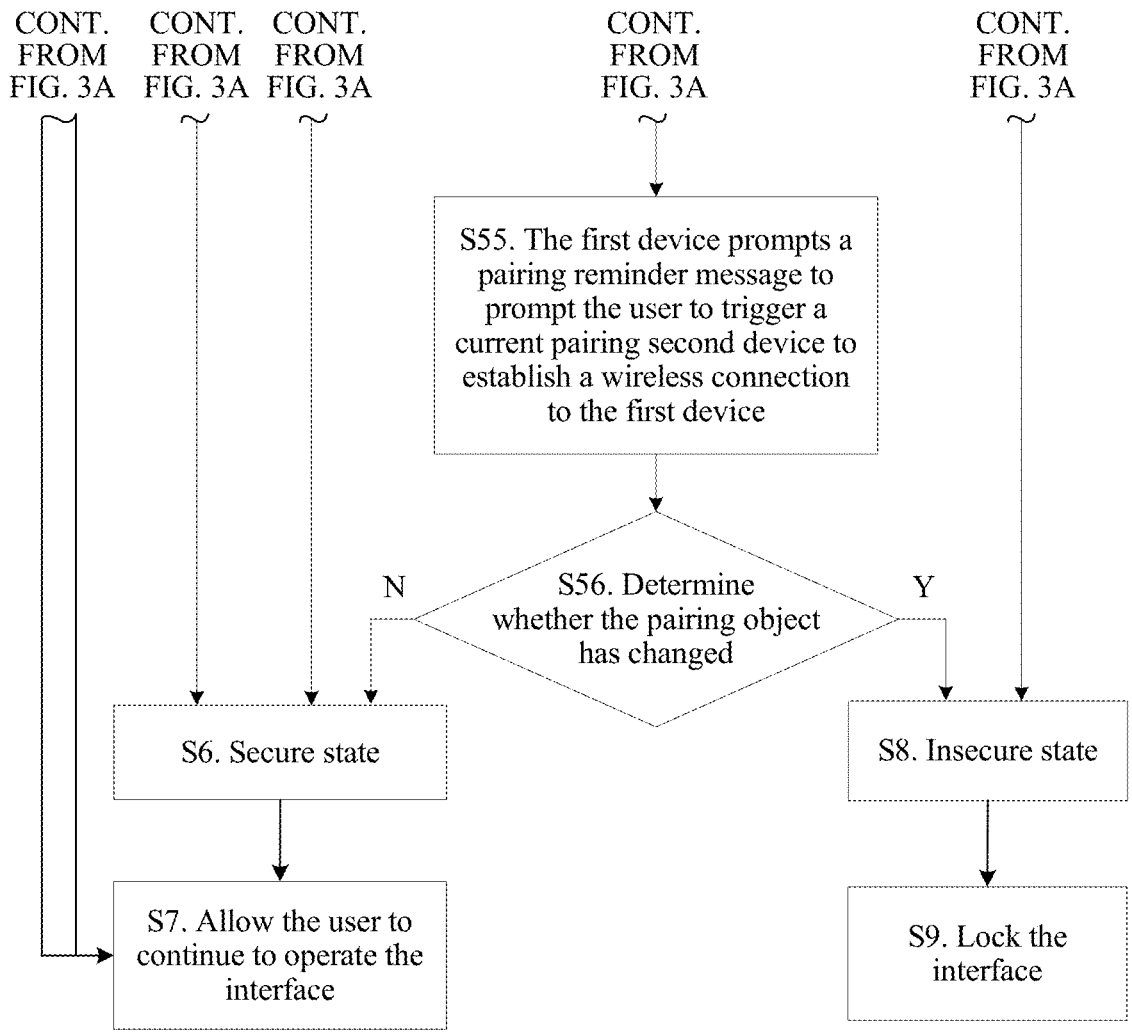

This embodiment of the present invention provides a security verification method. As shown in FIG. 3A and FIG. 3B, the method includes the following steps:

S1. When a user operates an interface of a first device, the first device receives a user operation instruction by using an input component 105. The instruction includes information about the interface operated by the user.

It should be noted that, the interface herein may be a system interface of the first device, a setting interface of the first device, or an interface of an application installed on the first device, and this is not limited herein.

S2. A processor 101 of the first device may determine, based on the information about the interface, whether the interface is an access-restricted interface.

The access-restricted interface herein may be a setting page of the first device. For example, if the user does not want another person to change a configuration parameter of the first device, the setting page of the first device may be defined as an access-restricted page. The access-restricted page may also be an interface of an application, such as a page of a payment application.

If the interface is not an access-restricted interface, the user is allowed to continue to operate the page, that is, step S7 is performed; or if the interface is an access-restricted interface, step S3 is performed.

S3. The processor 101 of the first device determines whether a security verification function is enabled.

If the security verification function is enabled, step S4 is performed, or if the security verification function is not enabled, step S7 is performed, and the user is allowed to continue to operate the page.

S4. The processor 101 of the first device determines a wearing status of the first device within a verification time window based on a monitoring result of a sensor 103, and/or determines a pairing status of the first device within the verification time window based on a monitoring result of a near field communication chip 104.

It should be noted that, herein the wearing status includes a worn state or a non-worn state, and the pairing status includes that a pairing object has changed or that a pairing object remains unchanged. The verification time window is a time interval between a moment at which the security verification function of the first device is enabled for the first time and a moment at which the user operates the application. Alternatively, if security verification has been performed on the first device before the user operates the application and a verification result is a secure state, the verification time window in this case is a time interval between a moment at which the first device is verified to be in the secure state and a moment at which the user operates the application.

In addition, if the first device is worn all the time within the verification time window or a time period within the verification time window and during which the first device is taken off is less than a threshold (such as 2 minutes), it is considered that the first device is in the worn state within the verification time window. If it is detected that a time period within the verification time window and during which the first device is not worn is greater than the threshold, it is considered that the first device is in the non-worn state within the verification time window.

Further, the first device may determine, based on the wearing status and the pairing status that are determined in step S4, whether the first device is in the secure state, which specifically includes the following steps:

S51. Perform step S6 if the first device is in the worn state within the verification time window.

It should be noted that if the first device is in the worn state within the verification time window, it may be considered that the first device is not lost or stolen and is in the secure state, and a user that currently operates the first device may be the user of the first device. Therefore, step S6 is performed to determine that the first device is in the secure state.

S52. Perform step S6 if the first device is in the paired state within the verification time window and a pairing object of the first device remains unchanged.

Specifically, the near field communication chip 104 of the first device records information about a second device that establishes a near field communication connection to the first device, for example, an SN, a MAC address, or an IMEI of the second device, or may record user information corresponding to the second device, that is, account information or an identity used for logging in to a management application program corresponding to the first device. That is, regardless of whether the first device is in the worn state, it is considered that the first device is in the secure state provided that the information about the paired second device or the paired user information remains unchanged.

Further, the processor 101 of the first device may determine, based on the information that is about the second device and that is recorded by the near field communication chip 104, whether the pairing object of the first device has changed, that is, determine whether the second device paired with the first device has changed or whether the user information paired with the first device has changed.

In a specific implementation, the processor 101 determines whether a current pairing second device is a second device paired with the first device when the first device is in the secure state at a latest time (that is, a second device paired with the first device when the first device is in the secure state during latest verification), or whether currently paired user information is previously paired user information.

S53. Perform step S8 if the first device is in the non-worn state and the paired state within the verification time window and the pairing object of the first device has changed.

It should be noted that if the first device is in the worn state within the verification time window, it may be considered that the first device is not lost or stolen and is in the secure state, and a user that currently operates the first device may be the user of the first device. Therefore, step S6 is performed to determine that the first device is in the insecure state.

It should be noted that, if the first device is in the non-worn state and the paired state within the verification time window, and the pairing object of the first device remains unchanged, it is considered that the first device is still in the secure state.

S54. Perform step S55 if the first device is in the non-worn state and the unpaired state within the verification time window.

It should be noted that if the first device is in the non-worn state within the verification time window, the first device may be stolen or obtained by another person. In addition, the near field communication connection between the first device and the second device is disconnected (for example, a Bluetooth function is disabled). In this case, the first device cannot confirm whether the second device paired with the first device has changed, and needs to establish a connection to the second device to obtain information about the second device (or user information entered by a user into a login interface of a management application program of the second device), so as to determine, based on the obtained information, whether the pairing object of the first device has changed.

S55. The first device prompts a pairing reminder message by using an output component, so as to prompt the user to trigger a current pairing second device to establish a wireless connection to the first device.

Figure 4:
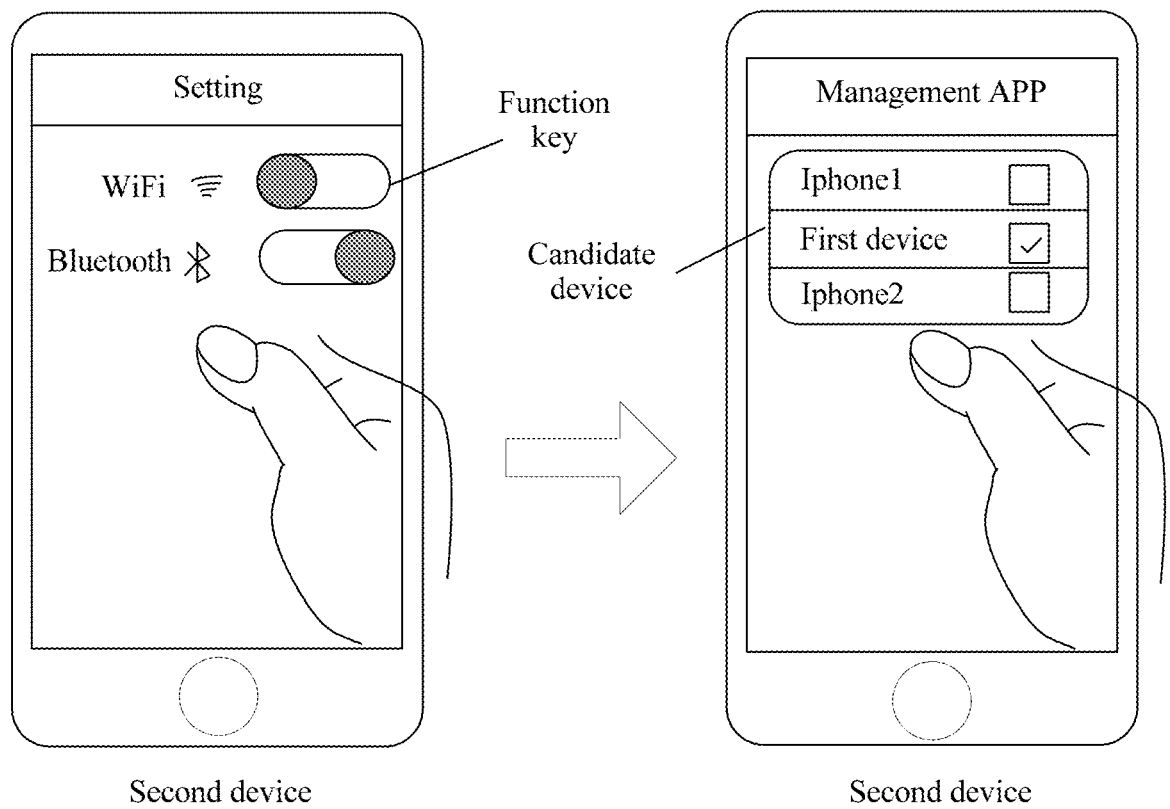
FIG. 4 is a schematic diagram of obtaining information about a current pairing second device by a first device according to an embodiment of the present invention.

If the security verification function of the first device is enabled for the first time (or a latest security verification result is the secure state), the first device records information about a paired second device. In this case, security verification needs to be performed on the first device based on the recorded information about the second device. For example, content of the message may be prompting the user to trigger the second device to establish a connection to the first device, for example, "Use Bluetooth of a mobile phone to connect the wearable device for further use". To continue to use the first device, the user establishes a connection between the second device and the first device based on the prompt. In this way, the first device obtains the information about the current pairing second device. Specifically, as shown in FIG. 4, a current user may tap a Bluetooth function key on a setting page of the current pairing second device to trigger a Bluetooth connection, select the first device from candidate devices, and establish a Bluetooth connection to the first device. In this process, the first device can obtain information about a current initially paired terminal.

Figure 5:
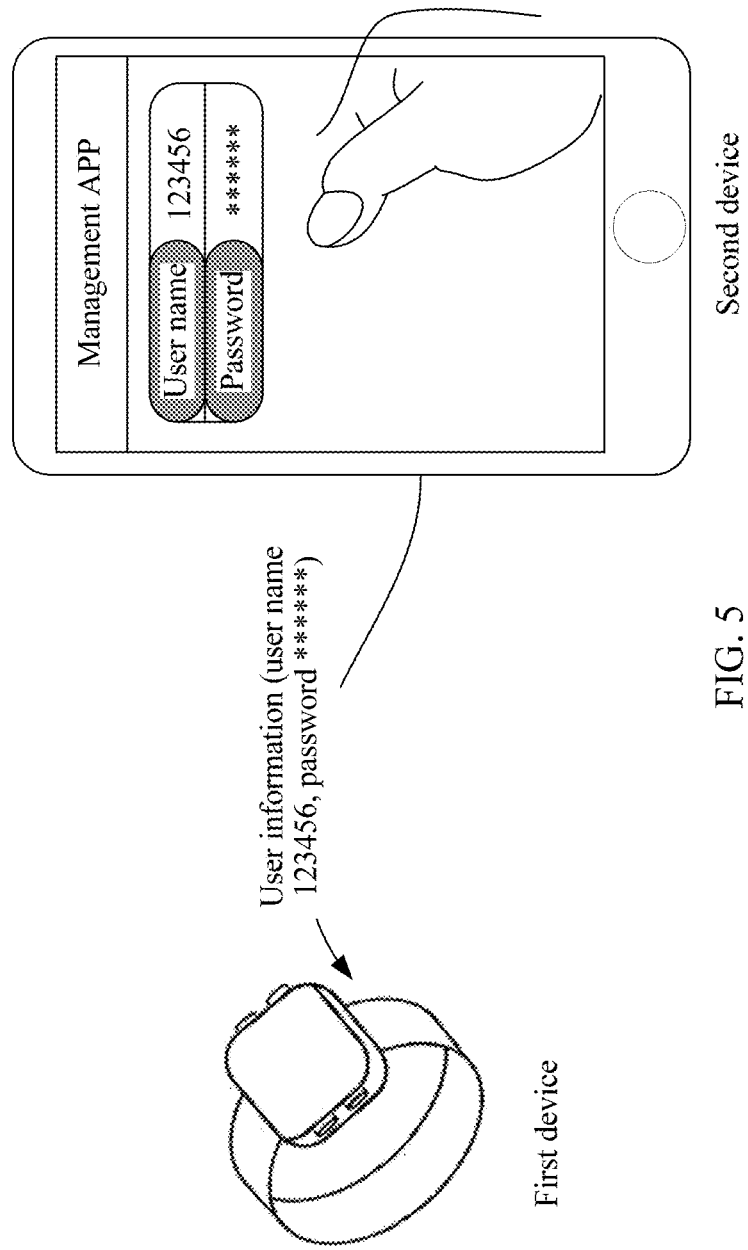
FIG. 5 is a schematic diagram of obtaining user information by a first device according to an embodiment of the present invention.

When the security verification function of the first device is enabled for the first time (or a previous security verification result is the secure state), if the first device records the user information corresponding to the paired second device (that is, the user information entered by the user when the user logs in to the management application program corresponding to the first device), in this case, security verification needs to be performed on the first device based on the recorded user information. In this case, content of a verification enabling message may be "Enter user information to log in to a management application program of the mobile phone", for example, "Enter a user name and a password to log in to a  band APP to use a  band". Certainly, if the wearable device is lost and obtained by another person, the another person first needs to download a management APP on a current initially paired terminal (different from the initially paired terminal) to use the wearable device. To continue to use the first device, the user establishes a connection between the second device and the first device based on the prompt, and enters the user information on a login page of a management application program of the current pairing second device. In this way, the first device obtains the user information corresponding to the current pairing second device. Specifically, as shown in FIG. 5, the current user may enter the user information on the login page of the management application program of the current pairing second device, and the management application program may invoke an interface of the terminal and send the user information to the first device by using the wireless connection between the second device and the second device. In this process, the first device can obtain the user information entered by the current user.

In a specific implementation, a first device with a screen may display a pairing reminder message, and a first device without a screen may prompt a voice pairing reminder message.

It should be noted that the sensor 103 transmits a recorded wearing status to the processor of the first device. After the processor verifies that the first device is in the secure state, the processor refreshes the recorded wearing status to accurately obtain the wearing status within the verification time window.

S56. The processor 101 of the first device determines whether the pairing object of the first device has changed.

In a specific implementation, the first device determines whether the information about the current pairing second device is the same as information about the initially paired second device (that is, the second device paired with the first device when the first device is in the secure state during previous verification). If the information about the current pairing second device is the same as the information about the initially paired second device, it is determined that the pairing object of the first device remains unchanged, or if the information about the current pairing second device is different from the information about the initially paired second device, it is determined that the pairing object of the first device has changed.

Alternatively, the first device determines whether the user information corresponding to the current pairing second device is the same as user information corresponding to the initially paired second device. If the user information corresponding to the current pairing second device is the same as the user information corresponding to the initially paired second device, it is determined that the pairing object of the first device remains unchanged, or if the user information corresponding to the current pairing second device is different from the user information corresponding to the initially paired second device, it is determined that the pairing object of the first device has changed. The user information corresponding to the current pairing second device is the user information entered by the user into the management application program of the current pairing second device, and the user information corresponding to the initially paired second device is user information entered by a user into a management application program of the initially paired second device.

Step S6 is performed if it is determined that the pairing object of the first device remains unchanged. Step S8 is performed if it is determined that the pairing object of the first device remains unchanged.

S6. Determine that the first device is in the secure state.
S7. Allow the user to continue to operate the interface.
S8. Determine that the first device is in the insecure state.
S9. Lock the interface.

The foregoing interface operated by the user is locked. Specifically, locking the interface may be exiting the interface. Alternatively, when the interface is an interface of an application, an icon of the application may be hidden, and an operation of tapping the icon of the application by the user is not responded. Alternatively, the first device may be locked, and does not respond to an operation performed by the user on the first device.

According to the security verification method provided in this embodiment of the present invention, the wearing status of the first device is monitored by using the sensor of the device, and the pairing status of the first device is monitored by using the near field communication chip. When the user operates an access-restricted interface of the first device, the wearing status or the pairing status of the first device within a time period may be determined to avoid a privacy disclosure and a capital loss caused because the device is lost, so as to determine, based on the wearing status or the pairing status of the first device, whether the first device is in the secure state. It can be learned that a configuration requirement on the wearable device is not high in the verification method, and identity verification can be performed on a user of the device by using a wearing monitoring module and a wireless connection module (for example, a Bluetooth module) configured on most devices. The method is applicable to most wearable devices, especially a low-configuration device without a screen, and may be used to verify a user identity, so as to significantly avoid a user loss after such wearable devices are lost or stolen.

It should be noted that the memory in this embodiment of the present invention may include a volatile memory such as an NVRAM (Nonvolatile Random Access Memory, nonvolatile random access memory), a PRAM (Phase Change RAM, phase change random access memory), or an MRAM (Magnetoresistive Random Access Memory, magnetoresistive random access memory). The memory may further include a nonvolatile memory such as at least one magnetic disk storage component, an EEPROM (Electrically Erasable Programmable Read-Only Memory, electrically erasable programmable read-only memory), or a flash component such as a NOR flash memory (NOR flash memory) or a NAND flash memory (NAND flash memory). The nonvolatile memory stores an operating system and an application program that are executed by the processor. The processor loads, from the non-volatile memory, a running program and data to the memory, and stores data content in a massive storage apparatus.

The memory may exist independently and is connected to the processor by using a system bus, or the memory may be integrated with the processor.

The processor is a control center of the first device. The processor connects all parts of the entire first device by using various interfaces and lines, and performs various functions of the first device and processes data by running or executing a software program and/or an application module stored in the memory and invoking data stored in the memory, so as to perform overall monitoring on the first device.

The processor may include only a CPU, or may be a combination of a CPU, a GPU (Graphic Processing Unit, graphic processing unit), a DSP, and a control chip (such as a baseband chip) in a communications unit. In this implementation of this application, the CPU may include a single computing core, or may include a plurality of computing cores. The system bus may be an ISA (Industry Standard Architecture, industry standard architecture) bus, a PCI (Peripheral Component Interconnect, peripheral component interconnect) bus, or an EISA (Extended Industry Standard Architecture, extended industry standard architecture) bus, or the like. The system bus may be classified into an address bus, a data bus, a control bus, and the like.

Further, the first device may further include a power supply, configured to supply power to different components of the first device to maintain running of the first device. Generally, the power supply may be a built-in battery, for example, a common lithium-ion battery or a nickel-metal hydride battery; or may be an external power supply that directly supplies power to the first device, for example, an AC (Alternating Current, alternating current) adapter. In some implementations of this application, the power supply may be further defined in a wider scope, for example, may further include a power management system, a charging system, a power failure detection circuit, a power converter or inverter, a power status indicator (such as a light emitting diode), and any other components related to power generation, management, and distribution of the first device.

Embodiment 2

Figure 6:
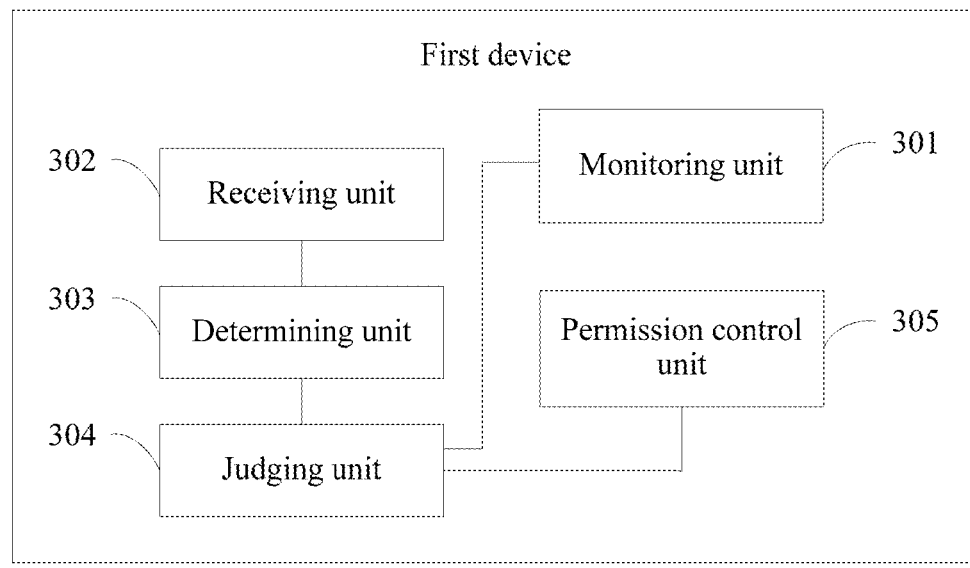
FIG. 6 is a structural block diagram of a first device according to an embodiment of the present invention.

This embodiment of the present invention is implemented on a basis of Embodiment 1, and provides a first device. As shown in FIG. 6, the first device includes: a monitoring unit 301, a receiving unit 302, a determining unit 303, a judging unit 304, and a permission control unit 305.

The monitoring unit 301 is configured to monitor pairing status of the first device and a second device and/or a wearing status of the first device.

The receiving unit 302 is configured to receive a user operation instruction, where the user operation instruction includes information about an interface operated by a user.

The determining unit 303 is configured to: when determining, based on the information about the interface, that the interface is an access-restricted interface, determine a wearing status and/or a pairing status of the first device within a verification time window.

The judging unit 304 is configured to determine, based on the wearing status and/or the pairing status within the verification time window and determined by the determining unit, whether the first device is in a secure state.

The permission control unit 305 is configured to lock the interface when the judging unit determines that the first device is in an insecure state, or respond to the user operation instruction when the judging unit determines that the first device is in the secure state.

It should be noted that the verification time window is duration between a moment at which the user operation instruction is received and a latest moment at which it is determined that the first device is in the secure state, or duration between a moment at which the user operation instruction is received and a moment at which a security verification function of the first device is enabled for the first time.

Further, the judging unit 304 is specifically configured to: if the first device is in a worn state within the verification time window, determine that the first device is in the secure state.

The judging unit 304 is specifically configured to: if the first device is in a paired state within the verification time window, determine whether a pairing object of the first device has changed; and if the pairing object of the first device remains unchanged, determine that the first device is in the secure state; or if the pairing object of the first device has changed, determine that the first device is in the insecure state.

Figure 7:
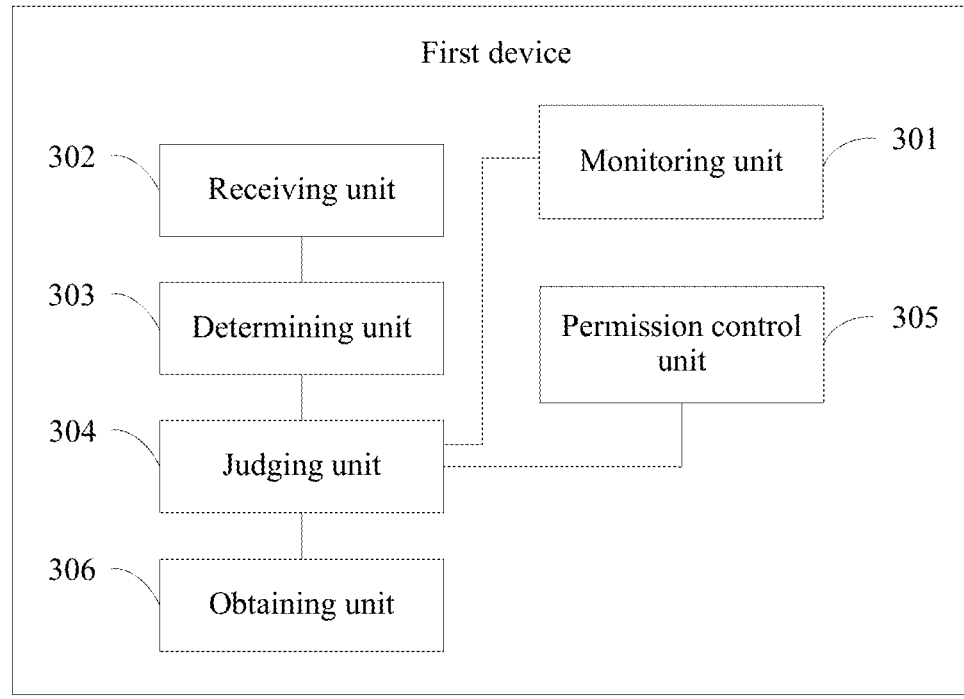
FIG. 7 is another structural block diagram of a first device according to an embodiment of the present invention.

The judging unit 304 is specifically configured to: if the first device is in a non-worn state and a paired state within the verification time window, determine whether a pairing object of the first device has changed; and if determining that the pairing object of the first device remains unchanged, determine that the first device is in the secure state; or if determining that the pairing object of the first device has changed, determine that the first device is in the insecure state As shown in FIG. 7, the first device further includes an obtaining unit 306.

If the judging unit 304 specifically determines that the first device is in a non-worn state and an unpaired state within the verification time window, the obtaining unit 306 is configured to obtain information about a current pairing object.

The judging unit 304 is further configured to: determine, based on the information about the current pairing object, whether a pairing object of the first device has changed; and if determining that the pairing object of the first device has changed, determine that the first device is in the insecure state; or if determining that the pairing object of the first device remains unchanged, determine that the first device is in the secure state.

The obtaining unit 306 is specifically configured to: prompt a pairing reminder message, where the pairing reminder message is used to prompt the user to trigger a current pairing second device to establish a wireless connection to the first device; establish a wireless connection to the current pairing second device; and receive the information that is about the current pairing object and that is sent by the current pairing second device, where the information about the current pairing object is information about the current pairing second device or user information corresponding to the current pairing second device.

The judging unit 304 is specifically configured to: determine whether the information about the current pairing object is the same as information about an initial pairing object; and if the information about the current pairing object is the same as the information about the initial pairing object, determine that the pairing object of the first device remains unchanged; or if the information about the current pairing object is different from the information about the initial pairing object, determine that the pairing object of the first device has changed.

It should be noted that if the information about the initial pairing object is information about a second device initially paired with the first device, the information about the current pairing object is the information about the current pairing second device; or if the information about the initial pairing object is user information corresponding to a second device initially paired with the first device, the information about the current pairing object is the user information corresponding to the current pairing second device.

The first device provided in this embodiment of the present invention may monitor the wearing status of the device and the pairing status of the first device and the second device. When the user operates an access-restricted interface of the first device, the wearing status or the pairing status of the first device within a time period may be determined to avoid a privacy disclosure and a capital loss caused because the device is lost, so as to determine, based on the wearing status or the pairing status of the first device, whether the first device is in the secure state. The interface operated by the user is locked when it is determined that the first device is in the insecure state, and the user operation instruction is responded to when it is determined that the first device is in the secure state. It can be learned that a configuration requirement on the wearable device is not high in the verification method, and identity verification can be performed on a user of the device by using a wearing monitoring module and a wireless connection module (for example, a Bluetooth module) configured on most devices. The method is applicable to most wearable devices, especially a low-configuration device without a screen, and may be used to verify a user identity, so as to significantly avoid a user loss after such wearable devices are lost or stolen.

It may be clearly understood by a person skilled in the art that, for the purpose of convenient and brief description, division of the foregoing function modules is taken as an example for illustration. In actual application, the foregoing functions can be allocated to different function modules and implemented based on a requirement, that is, an inner structure of a mobile device is divided into different function modules to implement all or part of the functions described above. For a detailed working process of the foregoing system, mobile device, and unit, reference may be made to a corresponding process in the foregoing method embodiments, and details are not described herein again.

In the several embodiments provided in this application, it should be understood that the disclosed system, mobile device, and method may be implemented in other manners. For example, the described mobile device embodiment is merely an example. For example, the module or unit division is merely logical function division and may be other division in an actual implementation. For example, a plurality of units or components may be combined or integrated into another system, or some features may be ignored or not performed. In addition, the displayed or discussed mutual couplings or direct couplings or communication connections may be implemented through some interfaces. The indirect couplings or communication connections between the mobile devices or units may be implemented in electronic, mechanical, or other forms.

The units described as separate parts may or may not be physically separate, and parts displayed as units may or may not be physical units, may be located in one position, or may be distributed on a plurality of network units. Some or all of the units may be selected based on actual requirements to achieve the objectives of the solutions of the embodiments.

In addition, functional units in the embodiments of this application may be integrated into one processing unit, or each of the units may exist alone physically, or two or more units are integrated into one unit. The integrated unit may be implemented in a form of hardware, or may be implemented in a form of a software functional unit.

When the integrated unit is implemented in the form of a software functional unit and sold or used as an independent product, the integrated unit may be stored in a computer-readable storage medium. Based on such an understanding, the technical solutions of this application essentially, or the part contributing to the prior art, or all or a part of the technical solutions may be implemented in the form of a software product. The software product is stored in a storage medium and includes several instructions for instructing a computer device (which may be a personal computer, a server, a network device, or the like) or a processor (processor) to perform all or a part of the steps of the methods described in the embodiments of this application. The foregoing storage medium includes: any medium that can store program code, such as a USB flash drive (Universal Serial Bus flash drive, Universal Serial Bus flash drive), a removable hard disk, a ROM, a RAM, a magnetic disk, or an optical disc.

The foregoing descriptions are merely specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. A security verification method, comprising:
monitoring, by a first device, a pairing status of the first device and a second device and/or a wearing status of the first device;
receiving, by the first device, a user operation instruction, wherein the user operation instruction comprises information about an interface operated by a user;
determining a wearing status and/or a pairing status of the first device within a verification time window, when the first device determines, based on the information about the interface, that the interface is an access-restricted interface;
determining, by the first device based on the wearing status and/or the pairing status within the verification time window, whether the first device is in a secure state; and
locking the interface if the first device is in an insecure state; or responding to the user operation instruction if the first device is in the secure state; wherein
the verification time window is duration between a moment at which the user operation instruction is received and a latest moment at which it is determined that the first device is in the secure state, or duration between a moment at which the user operation instruction is received and a moment at which a security verification function of the first device is enabled for the first time; wherein
the determining, by the first device based on the wearing status and/or the pairing status within the verification time window, whether the first device is in a secure state specifically comprises: if the first device is in a non-worn state and an unpaired state within the verification time window;
obtaining, by the first device, information about a current pairing object, and determining, based on the information about the current pairing object, whether a pairing object of the first device has changed; and
if it is determined that the pairing object of the first device has changed, determining that the first device is in the insecure state; or if it is determined that the pairing object of the first device remains unchanged, determining that the first device is in the secure state.

2. The method according to claim 1, wherein the determining, by the first device based on the wearing status or the pairing status within the verification time window, whether the first device is in a secure state specifically comprises:
if the first device is in a worn state within the verification time window, determining that the first device is in the secure state.

3. The method according to claim 1, wherein the determining, by the first device based on the wearing status and/or the pairing status within the verification time window, whether the first device is in a secure state specifically comprises:
if the first device is in a paired state within the verification time window, determining whether a pairing object of the first device has changed; and
if the pairing object of the first device remains unchanged, determining that the first device is in the secure state; or if the pairing object of the first device has changed, determining that the first device is in the insecure state.

4. The method according to claim 1, wherein the determining, by the first device based on the wearing status and/or the pairing status within the verification time window, whether the first device is in a secure state specifically comprises:
if the first device is in a non-worn state and a paired state within the verification time window, determining whether a pairing object of the first device has changed; and
if the pairing object of the first device remains unchanged, determining that the first device is in the secure state; or if the pairing object of the first device has changed, determining that the first device is in the insecure state.

5. The method according to claim 1, wherein the obtaining, by the first device, information about a current pairing object specifically comprises: prompting, by the first device, a pairing reminder message, wherein the pairing reminder message is used to prompt the user to trigger a current pairing second device to establish a wireless connection to the first device; establishing, by the first device, a wireless connection to the current pairing second device, and receiving the information that is about the current pairing object and that is sent by the current pairing second device, wherein the information about the current pairing object is information about the current pairing second device or user information corresponding to the current pairing second device.

6. The method according to claim 5, wherein the determining, by the first device based on the information about the current pairing object, whether a pairing object of the first device has changed specifically comprises:
determining, by the first device, whether the information about the current pairing object is the same as information about an initial pairing object; and
if the information about the current pairing object is the same as the information about the initial pairing object, determining that the pairing object of the first device remains unchanged; or if the information about the current pairing object is different from the information about the initial pairing object, determining that the pairing object of the first device has changed.

7. The method according to claim 6, wherein if the information about the initial pairing object is information about a second device initially paired with the first device, the information about the current pairing object is the information about the current pairing second device; or if the information about the initial pairing object is user information corresponding to a second device initially paired with the first device, the information about the current pairing object is the user information corresponding to the current pairing second device.

8. A first device, comprising:
a near field communication chip, configured to monitor a pairing status of the first device and a second device; and/or a sensor, configured to monitor a wearing status of the first device;
an input component, configured to receive a user operation instruction, wherein the user operation instruction comprises information about an interface operated by a user; and
a processor, configured to: when determining, based on the information about the interface, that the interface is an access-restricted interface, determine a wearing status and/or a pairing status of the first device within a verification time window; determine, based on the wearing status and/or the pairing status within the verification time window and determined by a determining unit, whether the first device is in a secure state; and lock the interface when a judging unit determines that the first device is in an insecure state, or respond to the user operation instruction when the judging unit determines that the first device is in the secure state; wherein
the verification time window is duration between a moment at which the user operation instruction is received and a latest moment at which it is determined that the first device is in the secure state, or duration between a moment at which the user operation instruction is received and a moment at which a security verification function of the first device is enabled for the first time; wherein
the processor is specifically configured to: if the first device is in a non-worn state and an unpaired state within the verification time window, obtain information about a current airing object; and
the processor is further configured to: determine, based on the information about the current pairing object, whether a pairing, object of the first device has changed; and if the pairing object of the first device has changed determine that the first device is in the insecure state; or if the pairing object of the first device remains unchanged, the first device is in the secure state.

9. The first device according to claim 8, wherein the processor is specifically configured to: if the first device is in a worn state within the verification time window, determine that the first device is in the secure state.

10. The first device according to claim 8, wherein the processor is specifically configured to: if the first device is in a paired state within the verification time window, determine whether a pairing object of the first device has changed; and
if the pairing object of the first device remains unchanged, determine that the first device is in the secure state; or if the pairing object of the first device has changed, determine that the first device is in the insecure state.

11. The first device according to claim 8, wherein the processor is specifically configured to:
if the first device is in a non-worn state and a paired state within the verification time window, determine whether a pairing object of the first device has changed; and
if the pairing object of the first device remains unchanged, determine that the first device is in the secure state; or if the pairing object of the first device has changed, the first device is in the insecure state.

12. The first device according to claim 8, further comprising an output component, wherein the output component k specifically configured to prompt a pairing reminder message, wherein the pairing reminder message is used to prompt the user to trigger a current pairing second device to establish a wireless connection to the first device; and the near field communication chip is configured to establish a wireless connection to the current pairing second device, and receive the information that is about the current pairing object and that is sent by the current pairing second device, wherein the information about the current pairing object is information about the current pairing second device or user information corresponding to the current pairing second device.

13. The first device according to claim 12, wherein the processor is specifically configured to: determine whether the information about the current pairing object is the same as information about an initial pairing object; and if the information about the current pairing object is the same as the information about the initial pairing object, determine that the pairing object of the first device remains unchanged; or if the information about the current pairing object is different from the information about the initial pairing object, determine that the pairing object of the first device has changed.

14. The first device according to claim 13, wherein if the information about the initial pairing object is information about a second device initially paired with the first device, the information about the current pairing object is the information about the current pairing second device; or if the information about the initial pairing object is user information corresponding to a second device initially paired with the first device, the information about the current pairing object is the user information corresponding to the current pairing second device.

15. A computer program product, wherein the product comprising:

a near field communication chip, configured to monitor a pairing status of the first device and a second device; and/or a sensor, configured to monitor a wearing status of the first device, an input component, configured to receive a user operation instruction, wherein the user operation instruction comprises information about an interface operated by a user; and a processor, configured to: when determining, based on the information about the interface, that the interface is an access-restricted interface, determine a wearing status and/or a pairing status of the first device within a verification time window; determine, based on the wearing status and/or the pairing status within the verification time window and determined by a determining unit, whether the first device is in a secure state; and lock the interface when a judging unit determines that the first device is in an insecure state, or respond to the user operation instruction when the judging unit determines that the first device is in the secure state; wherein the verification time window is duration between a moment at which the user operation instruction is received and a latest moment at which it is determined that the first device is in the secure state, or duration between a moment at which the user operation instruction is received and a moment at which a security verification function of the first device is enabled for the first time; wherein the determine the wearing status and/or the pairing status within the verification time window, whether the first device is in a secure state specifically comprises: if the first device kin a non-worn state and an unpaired state within the verification time window;

obtaining information about a current pairing object, and determining, based on the information about the current pairing object, whether a pairing object of the first device has changed; and if it is determined that the pairing object of the first device has changed, determining that the first device is in the insecure state; or if it is determined that the pairing object of the first device remains unchanged, determining that the first device is in the secure state.

* * * * *